United States Patent [19]

Nakahara et al.

[11] 4,250,312
[45] Feb. 10, 1981

[54] PROCESS FOR PREPARING 4-PIPERIDONE SPIROKETAL COMPOUNDS

[75] Inventors: Yutaka Nakahara, Iwatsuki; Naohiro Kubota, Ageo; Toshihiro Shibata, Omiya, all of Japan

[73] Assignee: Argus Chemical Corp., Brooklyn, N.Y.

[21] Appl. No.: 108,137

[22] Filed: Dec. 28, 1979

[51] Int. Cl.³ .................................. C07D 405/04
[52] U.S. Cl. .................................... 546/19
[58] Field of Search .................... 546/19, 242

[56] References Cited

U.S. PATENT DOCUMENTS

| | | |
|---|---|---|
| 3,899,464 | 8/1975 | Murayama ............................ 546/19 |
| 4,096,114 | 6/1978 | Minagawa et al. .................... 546/19 |
| 4,105,625 | 8/1978 | Minagawa et al. .................... 546/19 |
| 4,115,476 | 9/1978 | Minagawa et al. .................... 546/19 |
| 4,116,927 | 9/1978 | Minagawa et al. .................... 546/19 |
| 4,118,369 | 10/1978 | Minagawa et al. .................... 546/19 |
| 4,136,081 | 1/1979 | Minagawa et al. .................... 546/19 |

*Primary Examiner*—Henry R. Jiles
*Assistant Examiner*—Robert T. Bond
*Attorney, Agent, or Firm*—Otto S. Kauder

[57] ABSTRACT

A 2,2,6,6-tetramethyl-4-piperidone spiroketal carbinol compound of Formula I

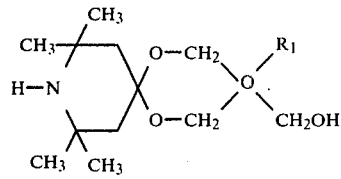

in which $R_1$ represents an alkyl group having from one to six carbon atoms, is prepared by heating a trimethylolalkane compound having the formula $R_1$—C(CH$_2$OH)$_3$ with a 2,2,6,6-tetramethyl-4-piperidone ketal compound of Formula II

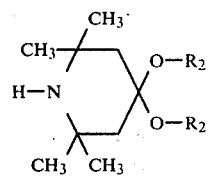

in which $R_2$ represents an alkyl group having from one to twelve carbon atoms or an ether-interrupted alkyl group having from three to twelve carbon atoms and from one to two ether oxygen atoms, removing alcohol $R_2$OH, and recovering 2,2,6,6-tetramethyl-4-piperidone spiroketal carbinol compound of Formula I.

12 Claims, No Drawings

PROCESS FOR PREPARING 4-PIPERIDONE SPIROKETAL COMPOUNDS

BACKGROUND OF THE INVENTION

This invention relates to a new process for preparing 4-piperidone spiroketal compounds in excellent yield and purity.

Hindered piperidine alcohol compounds having Formula I, which can be named 2,2,6,6-tetramethyl-4-piperidone spiroketal carbinol compounds, or more systematically 9-aza-3-hydroxymethyl-3-alkyl-8,8,10,10-tetramethyl-1,5-dioxaspiro(5,5) undecanes,

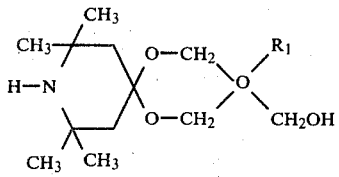

have been disclosed by K. Murayama in U.S. Pat. No. 3,899,464 of Aug. 12, 1975 as stabilizers able to protect synthetic polymers and plastics against the harmful effects of exposure to ultraviolet radiation and heat. Compounds of Formula I have also been disclosed to be valuable synthetic intermediates for the preparation of even better stabilizers by reaction of the compounds at the alcoholic hydroxyl group to form various derivatives. Outstandingly effective stabilizers among these derivatives are certain organic phosphite esters disclosed by M. Minagawa et al in U.S. Pat. No. 4,096,114 of June 20, 1978; hydroxyaliphatic dicarboxylic and tricarboxylic acid esters disclosed by M. Minagawa et al in U.S. Pat. No. 4,105,625 of Aug. 8, 1978; diol bis-carbonate esters disclosed by M. Minagawa et al in U.S. Pat. No. 4,115,476 of Sept. 19, 1978; butane-and butene-tricarboxylic acid esters diclosed by M. Minagawa et al in U.S. Pat. No. 4,116,927 of Sept. 26, 1978; heterocyclic carboxylic acid esters disclosed by M. Minagawa et al in U.S. Pat. No. 4,118,369 of Oct. 3, 1978; and aliphatic tetracarboxylic acid esters disclosed by M. Minagawa et al in U.S. Pat. No. 4,136,081 of Jan. 23, 1979.

Compounds of Formula I have hitherto been prepared as disclosed by Murayama by the reaction of a tetraalkyl-4-piperidone with a trimethylolalkane in the presence of an acid catalyst. However, the procedure has required long reaction times and the product was impure; in Murayama's description of this process no product yields are given.

Ketal derivatives of 4-piperidones have been known for some time, but no exchange reactions of 4-piperidone ketals with alcohols have been reported. P. Brookes and J. Walker in J. Chem. Soc. 1957, pages 3172–3175, disclosed the ready conversion of 1-n-butyl-4-piperidone hydrochloride to 1-n-butyl-4-piperidone dimethyl and diethyl ketal hydrochlorides by warming with methanol or ethanol respectively, the similar conversion of 1-benzyl-4-piperidone hydrochloride to 1-benzyl-4-piperidone diethyl ketal hydrochloride by warming with ethanol, and the ready conversion of 1-benzyl-4-piperidone diethyl ketal hydrochloride to 1-benzyl-4-piperidone hydrochloride by warming with hydrochloric acid, but noted that 1-n-butyl-4-piperidone dimethyl ketal hydrochloride was recovered unchanged after warming with ethanol. Thus no exchange of one alcohol for another in a piperidone ketal occurred under the conditions used by Brookes and Walker.

SUMMARY OF THE INVENTION

In accordance with this invention, a process for preparing a 2,2,6,6-tetramethyl-4-piperidone spiroketal carbinol compound having the Formula I

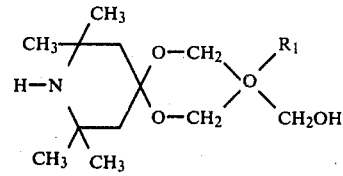

in which $R_1$ represents an alkyl group having from one to six carbon atoms, comprises the steps of heating in the presence of an acid catalyst a mixture of trimethylolalkane compound having the formula $R_1$—C(CH$_2$OH)$_3$ with a 2,2,6,6-tetramethyl-4-piperidone ketal compound having the Formula II

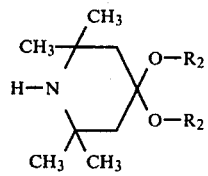

in which $R_2$ represents an alkyl group having from one to twelve carbon atoms or an ether-interrupted alkyl group having from three to twelve carbon atoms and from one to two ether oxygen atoms, removing alcohol $R_2$OH, and recovering 2,2,6,6-tetramethyl-4-piperidone spiroketal carbinol compound having Formula I from the mixture.

The carbinol compound of Formula I can be obtained according to this invention as the free base, or alternatively as an acid addition salt with any of the acids hydrochloric acid, sulfuric acid, phosphoric acid, hydrobromic acid, p-toluenesulfonic acid, acetic acid, and oxalic acid. Also, the 2,2,6,6-tetramethyl-4-piperidone ketal compound of Formula II can be supplied to the process of this invention as the free base or as an acid addition salt with any of the recited acids.

The process of the invention furnishes the carbinol compound of Formula I in less time and in greater purity as well as better yield than prior art processes.

DESCRIPTION OF THE PREFERRED EMBODIMENTS

In the 2,2,6,6-tetramethyl-4-piperidone spiroketal carbinol compound of Formula I, and in the trimethylolalkane starting material having the formula $R_1$—C(CH$_2$OH)$_3$, the alkyl group $R_1$ can be for example methyl, ethyl, propyl, isopropyl, n-butyl, isobutyl, n-pentyl, 3-methylbutyl, and n-hexyl. The substituent group $R_2$ in the 2,2,6,6-tetramethyl-4-piperidone ketal starting material having Formula II can be any of the alkyl groups $R_1$ as well as n-heptyl, n-octyl, isooctyl, 2-ethylhexyl, nonyl, n-decyl, isodecyl, undecyl and n-dodecyl. An ether-interrupted alkyl group $R_2$ can be 2-methoxyethyl, 2-ethoxyethyl, 2-isopropoxyethyl, 2-n-butoxyethyl, 2-isobutoxyethyl, 3-methoxybutyl, 3-methoxy- 3-methylbutyl, 2(2'-methoxyethoxy)ethyl, 2(2'-ethoxyethoxy)ethyl, and 2(2'-butoxyethoxy)ethyl.

In the process according to this invention, approximately equimolar proportions of the trimethylolalkane and 2,2,6,6-tetramethyl-4-piperidone ketal compound reactants are used, although an excess of either reactant can be used if desired. The reaction proceeds with generation of alcohol represented by the formula $R_2Oh$, in which $R_2$ is as defined above, and this alcohol is at some point separated from the desired carbinol compound of Formula I. Convenient techniques for accomplishing the removal of alcohol include partitioning the mixture between water and a water-immiscible solvent such as hexane or toluene, whereby the alcohol is enriched in the water phase and the carbinol compound Formula I in the solvent phase; crystallization of the carbinol compound of Formula I either as the free base or as an acid addition salt and separation of the crystals by filtration or centrifugation from the mother liquor containing the alcohol; or distillation from the reaction mixture after the reaction is finished, or intermittently or continuously while the reaction is proceeding. Distillation represents a particularly preferred technique for removing the alcohol.

Unlike prior art processes, the reaction in the process of this invention produces no water, and this is believed to be a beneficial feature. Modest amounts of water, however, can be tolerated in the mixture, up to about 2% by weight, without interfering with the process.

The 2,2,6,6-tetramethyl-4-piperidone spiroketal carbinol compound of Formula I, which can also be named according to systematic nomenclature as a 9-aza-3-hydroxymethyl-3-alkyl-8,8,10,10-tetramethyl-1,5-dioxaspiro(5,5)undecane, can be removed from the mixture in which it is produced as the free base or as an acid addition salt such as the hydrochloride. To recover the free base, the reaction mixture, in which the carbinol compound of Formula I can be present as an acid addition salt as a result of the use of a 2,2,6,6-tetramethyl-4-piperidone ketal acid addition salt starting material or of an acid catalyst in sufficient quantity, is treated with an excess of a base, which is preferably inorganic and can be used dry or in an aqueous solution. The common inorganic bases are suitable, such as anhydrous ammonia, lime, barium hydroxide and the alkali metal hydroxides and carbonates. The treatment with inorganic base results in the formation of inorganic salt, which can be present as a solid or as an aqueous solution, and an organic phase comprising the desired free base form of the carbinol compound of Formula I and any water-immiscible solvent present. Recovery of the carbinol compound of Formula I is then completed by drying the organic solution and concentrating it, suitably under reduced pressure, until crystallization of the carbinol occurs or to dryness. The crystals can then be collected for packing and shipping or for use in further synthesis by conventional methods.

In the process of this invention the use of an acid catalyst is helpful and is preferred. Suitable acid catalysts have an acid strength indicated by a pK not greater than 3, and include among other hydrochloric acid, sulfuric acid, phosphoric acid, and p-toluenesulfonic acid. The quantity of acid catalyst is suitably from 0.02 to 2 moles per mole of 2,2,6,6-tetramethyl-4-piperidone ketal reactant, preferably from 1.05 mole to 1.25 mole acid catalyst per mole of ketal as the free base.

The process of this invention is suitably carried out at any convenient temperature in the range from 20° to 300° C., preferably in the range from 60° to 200° C. An organic solvent can be used to facilitate mixing of the reactants and control of the temperature and rate of reaction. The solvent suitably has a boiling point in the range from 30° to 200° C., and can be a hydrocarbon such as benzene, toluene, xylene, ethylbenzene, cumene, pseudocumene, cymene, hexane, heptane, octane, or cyclohexanes; an ether such as diethyl ether or tetrahydrofurane; an amide such as dimethylformamide or dimethylacetamide; a lower aliphatic ketone such as acetone or methyl ethyl ketone, or a lower alcohol such as methanol or ethanol.

The process of this invention can be conveniently carried out at atmospheric pressure, but pressures greater or less than atmospheric can be applied if desired; for example a closed pressure vessel can be used to contain the reaction mixture with diethyl ether as solvent if it is desired to operate above its atmospheric boiling point.

The trimethylolalkane and 2,2,6,6-tetramethyl-4-piperidone ketal starting materials for the process of this invention are known and readily available chemicals. Trimethylolalkanes are industrial chemicals produced in large volume. 2,2,6,6-tetramethyl-4-piperidone ketals can be prepared by the reaction of alcohols $R_2OH$ (where $R_2$ is as defined above) with 2,2,6,6-tetramethyl-4-piperidone as disclosed, for example, by A. F. Casy, Experientia 1964, Vol. 20, pages 437–438, and by K. Murayama in U.S. Pat. No. 3,790,525 of Feb. 5, 1974.

EXAMPLE 1

Preparation of 9-aza-3-hydroxymethyl-3-ethyl-8,8,10,10-tetramethyl-1,5-dioxaspiro(5,5)undecane (compound of Formula I in which $R_1$ is ethyl). 2,2,6,6-Tetramethyl-4,4-bis(methoxyethoxy)piperidine hydrochloride 32.5 g (0.1 mole), trimethylolpropane 13.4 g (0.1 mole), p-toluene sulfonic acid 1.5 g and Solvesso 150 (Esso Standard; aromatic hydrocarbon mixture of a boiling rage 186° to 211° C.) 200 ml were heated at 90° C. 100 mmHg, for 10 hours while removing the generated methoxy ethanol. Then, 30 ml of 30% aq. NaOH was added, and the organic layer was washed with water and dried. The solvent was distilled off and the product was recrystallized from xylene and 25.5 g of white crystals of mp. 108°–109° C. was obtained. (Yield=94.1%)

The infrared spectrum and elemental analysis of the product corresponds to those of desired compound, as shown by infrared absorption at 3240 cm$^{-1}$ (N—H stretching frequency) and 1100 cm$^{-1}$ (C—O—C ketal frequency) and analysis for carbon, found 66.2% (calculated 66.4%); hydrogen, 10.8% (calculated 10.7%) and nitrogen 5.2% (calculated 5.2%)

These results show that the desired compound was successfully produced by the process of this invention in excellent yield and purity.

EXAMPLE 2

Preparation of 9-aza-3-hydroxymethyl-3-ethyl-8,8,10,10-tetramethyl-1,5-dioxaspiro(5,5)undecane from 2,2,6,6-tetramethyl-4,4-dimethoxypiperidine (compound of Formula II in which $R_2$ is methyl). 2,2,6,6-tetramethyl-4,4-dimethoxypiperidine 20.1 g (0.1 mole), trimethylolpropane 13.4 g (0.1 mole), p-toluenesulfonic acid 19 g and toluene 200 ml were heated at 90° C. for 10 hours while removing produced methanol.

Sodium hydroxide (30 ml of 30% aqueous solution) was added, and the product recovered as in Example 1 to give 23.5 g of white crystals, melting point 108°–109° C., representing 86.7% of the theoretical yield.

These results also show the production of the desired compound in excellent yield and purity according to this invention.

EXAMPLE 3

Preparation of 9-aza-3-hydroxymethyl-3-ethyl-8,8,10,10-tetramethyl-1,5-dioxaspiro(5,5)undecane hydrochloride. 2,2,6,6-Tetramethyl-4,4-bis(ethoxyethyl)-piperidine hydrochloride 35.3 g (0.1 mole), trimethylolpropane 13.4 g (0.1 mole) and Solvesso 150 200 ml were heated at 90° C. for 10 hours while bubbling HCl gas. After cooling, the resulting precipitate was filtered and then recrystallized from benzenebutanol, 29.6 g of white crystals of mp. 129°–137° C. was obtained. (Yield=96.3%).

These results show the successful preparation of the desired compound and recovery thereof as the hydrochloride addition salt in excellent yield and purity by the process of this invention.

EXAMPLE 4

Preparation of 9-aza-3-hydroxymethyl-3,8,8,10,10-pentamethyl-1,5-dioxaspiro(5,5)undecane (compound of Formula I in which $R_1$ is methyl). 2,2,6,6-Tetramethyl-4,4-bis(methoxyethoxy)piperidine hydrochloride 32.5 g (0.1 mole), trimethylolethane 12.0 g (0.1 mole), p-toluene sulfonic acid 1.5 g and xylene 200 ml were heated at 100° C., 100 mmHg for 8 hours while removing the by-product 2-methoxyethanol. The sodium hydroxide solution was added and the mixture treated as in Example 1, 24.0 g white crystals of mp. 125°–126° C. was obtained. (Yield=93.4%)

The infrared absorption spectrum showed absorption of 3240 cm$^{-1}$ and 1100 cm$^{-1}$ and analyzed for carbon, 65.3 (calculated 65.4), hydrogen 10.6 (calculated 10.5) and nitrogen 5.4 (calculated 5.4) percent.

The results of this experiment show the successful preparation of the desired compound by the process of this invention.

CONTROL EXAMPLE

Preparation of 9-aza-3hydroxymethyl-3-ethyl-8,8,10,10-tetramethyl-1,5-dioxaspiro(5,5)undecane by prior art process 2,2,6,6-Tetramethyl-4-piperidone p-toluenesulfonic acid salt 32.7 g (0.1 mole); trimethylolpropane 13.4 g (0.1 mole), p-toluenesulfonic acid 3 g and toluene 200 ml were refluxed for 10 hours while removing produced water.

Sodium hydroxide 30% aqueous solution was added to the mixture and from this point the procedure of Example 1 was followed to obtain 19.3 g (71.2% of theoretical yield) of the free base form of the desired compound as white crystals of melting point 106°–108° C.

These results show that the prior art process affords a lower yield of a less pure product than the process of this invention.

We claim:

1. A process for preparing a 2,2,6,6-tetramethyl-4-piperidone spiroketal carbinol compound having the Formula I

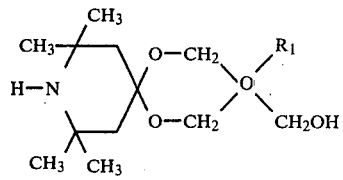

in which $R_1$ is an alkyl group having from one to six carbon atoms, comprising the steps of heating a mixture of trimethylolalkane compound having the formula $R_1$—C(CH$_2$OH)$_3$ and 2,2,6,6-tetramethyl-4-piperidine ketal compound having the Formula II

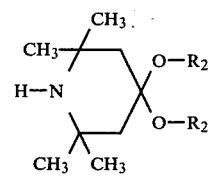

in which $R_2$ is an alkyl group having 1 to 12 carbon atoms or an ether-interrupted alkyl group having 3 to 12 carbon atoms and 1 to 2 ether oxygen atoms, or an acid addition salt thereof, removing alcohol having the formula $R_2OH$, and recovering 2,2,6,6-tetramethyl-4-piperidonespiroketal carbinol compound.

2. A process according to claim 1 in which $R_1$ is ethyl.

3. A process according to claim 1 in which $R_1$ is methyl.

4. A process according to claim 1 in which $R_2$ is methyl.

5. A process according to claim 1 in which $R_2$ is 2-methoxyethyl.

6. A process according to claim 1 in which $R_2$ is 2(2'-methoxyethoxy)ethyl.

7. A process according to claim 1 in which the reaction temperature is in the range from 60° to 200° C.

8. A process according to claim 1 in which a catalytic quantity of acid catalyst having a pK not exceeding 3 is present in the heated mixture.

9. A process according to claim 8 in which the acid catalyst is one or more of hydrochloric acid, sulfuric acid, phosphoric acid and p-toluenesulfonic acid.

10. A process according to claim 8 in which the quantity of catalyst is from 0.02 to 2 moles per mole of 2,2,6,6-tetramethyl-4-piperidone ketal compound.

11. A process according to claim 1 in which there is used an organic solvent having a boiling point in the range of 30° to 230° C.

12. A process according to claim 1 in wich alcohol $R_2OH$ is removed from the mixture by distillation.

* * * * *